United States Patent [19]

Karkhanis

[11] 4,330,623
[45] May 18, 1982

[54] PROCESS FOR SOLUBILIZATION OF GONOCOCCAL ANTIGEN

[75] Inventor: Yashwant D. Karkhanis, Fanwood, N.J.

[73] Assignee: Merck & Co., Inc., Rahway, N.J.

[21] Appl. No.: 122,533

[22] Filed: Feb. 19, 1980

[51] Int. Cl.³ .................. C12P 19/04; C12P 21/00
[52] U.S. Cl. ........................... 435/68; 435/101; 435/69; 435/272; 435/274; 435/871; 424/92
[58] Field of Search ............ 435/68, 101, 272, 69, 435/871, 274; 424/92

[56] References Cited

U.S. PATENT DOCUMENTS

| | | | |
|---|---|---|---|
| 3,855,197 | 12/1974 | Hirsch et al. | 435/871 |
| 4,007,265 | 1/1977 | Helting | 424/92 |
| 4,203,971 | 5/1980 | Buchanan | 424/92 |
| 4,220,638 | 9/1980 | Karkhanis et al. | 424/92 |
| 4,239,749 | 12/1980 | Buchanan | 424/92 |

OTHER PUBLICATIONS

Apicella et al., *Immunobiology of Neisseria gonorrhoeae*, Proceedings of American Society for Microbiology, San Francisco, Cal. 1978, p. 108.
Worthington Enzyme Manual, Trypsin (Bovine Pancrease), pp. 125–127, (1972).

*Primary Examiner*—Esther M. Kepplinger
*Attorney, Agent, or Firm*—Gabriel Lopez; Theresa Y. Cheng; Hesna J. Pfeiffer

[57] ABSTRACT

Gonococcal antigens are solubilized by a process involving trypsin-digestion.

4 Claims, No Drawings

PROCESS FOR SOLUBILIZATION OF GONOCOCCAL ANTIGEN

BACKGROUND OF THE INVENTION

The present invention relates to a process for the solubilization of gonococcal antigens, especially those isolated from the cell surface of *Neisseria gonorrhoeae*. For example, gonococcal lipopolysaccharides, $G_c$ antigens (a family of polysaccharides. See M. A. Apicella et. al, in Immunobiology of *Neisseria gonorrhoeae*, proceedings of a conference held in San Francisco, Calif., 1978, American Society for Microbiology, Washington, D.C., p. 108), or the antigenic complex as described in U.S. Patent Application Ser. No. 949,581 filed Oct. 12, 1978, now U.S. Pat. No. 4,220,638.

The solubilization of these antigens is essential to their capacity as a vaccine against *N. gonorrhoeae* for humans. This is because most of these antigens contain water-insoluble determinants such as protein or peptides. In order to inject a vaccine subcutaneously, intravenously or intramuscularly, it is necessary that the antigens which constitute the vaccine be substantially solubilized in a physiologically acceptable medium, for example sterile saline.

The solubilization process of the present invention involves trypsin digestion of the antigen. Although trypsin has been used to digest other bacterial antigens, it has not been used to solubilize gonococcal antigens isolated from *N. gonorrhoeae*.

Accordingly, it is an object of the present invention to provide a process for solubilization of the gonococcal antigens to be used in a vaccine against *N. gonorrhoeae*.

Still another object of the present invention is to provide a procedure for solubilizing gonococcal antigens as a means to facilitate the isolation and purification of the active peptides of the antigen in a water-soluble form.

DETAILED DESCRIPTION OF THE INVENTION

A $G_c$ antigen or an outermembrane antigenic complex, for example, the complex of U.S. application Ser. No. 949,581 which contains on a dry weight basis about 90-95% protein, about 7% lipopolysaccharide, about 2% carbohydrate and less than 1% of RNA, DNA and phospholipids, is suspended in a sufficient amount of an aqueous solution containing about 0.5 to 2.5 mmole/liter preferably 0.8 to 1.2 mmole/liter of sodium hydroxide at pH between 7 and 9. An appropriate amount of trypsin (TPCK-trypsin 1 mg/ml solution in water, Worthington Biochemical Corporation) is added portionwise and the resulting suspension is incubated at about 34° to 38° C. for about 1 to 5 hours or until the digestion is complete.

The trypsin digest is eluted with water through an affinity column packed with a gel material coupled with a trypsin inhibitor. For example, Ultrogel AcA34 ® (a gel which is an aqueous suspension of 3% polyacrylamide and 4% agarose) coupled with soybean trypsin inhibitor from Boehringer Mannheim Co.) as described in Science Tools, The LKB Instrument Journal, 25 18–21 (1978).

The resulting eluate is mixed with an equal volume of aqueous sodium chloride (about 0.1 to 0.5 N) and filtered to give the solubilized antigen in saline.

Upon dilution and sterilization, a solution of the solubilized antigen of a concentration of about 100 to 500 µg/ml is obtained and used for vaccination. The dosage usually varies from about 50 to 250 µg in 0.1 to 0.5 ml of sterile saline.

The following example illustrates this invention.

EXAMPLE 1

Lyophilized $G_c$ antigen (37.8 mg) is suspended in 8.0 ml of 0.001 N aqueous sodium hydroxide with a final pH of 7.8. The resulting suspension is prewarmed to 37° C. in a heater-block before 100 µg of TPCK-trypsin in 100 ml of water are added. The mixture is incubated at 37° C. for 50 min. followed by two additions of 130 µg of trypsin at 50 min. intervals. The total incubation time is about 150 minutes.

The trypsin digest is applied directly to a 2×4 cm column packed with Ultrogel AcA34 ® coupled with soybean trypsin inhibitor and preequilibrated with water. It is eluted with about 25 ml of water. The eluate (25 ml) is mixed with 25 ml of 0.3 N aq. sodium chloride and filtered to give a solution of about 0.76 mg/ml of the solubilized antigen.

What is claimed:

1. A process for the solubilization of gonococcal antigens in a physiologically acceptable medium comprising:
   (a) suspending the antigen in aqueous sodium hydroxide at pH 7–9;
   (b) completely digesting the suspension together with trypsin at 37° C.;
   (c) eluting the trypsin digest through an affinity column with water; and
   (d) diluting the eluate with a medium.

2. The process of claim 1 wherein the pH of step (a) is 7.8.

3. The process of claim 1 wherein the affinity column is packed with an aqueous suspension of 3% polyacrylamide and 4% agarose coupled with soybean trypsin inhibitor.

4. The process of claim 1 wherein the medium is aqueous sodium chloride.

* * * * *